United States Patent [19]

Ping-Fan

[11] Patent Number: 5,849,882
[45] Date of Patent: Dec. 15, 1998

[54] METHODS FOR THE PREPARATION OF BIOACTIVE PEPTIDES BY PROTEIN HYDROLYSIS

[75] Inventor: Rao Ping-Fan, Fuzhou, Fiji

[73] Assignee: BioEgg, L.L.C., Great Falls, Va.

[21] Appl. No.: 691,455

[22] Filed: Aug. 2, 1996

[51] Int. Cl.$^6$ .............................. A61K 38/01; C07K 1/12
[52] U.S. Cl. ......................... 530/407; 530/300; 530/343; 530/344
[58] Field of Search .................................... 530/300, 343, 530/344, 407

[56] References Cited

U.S. PATENT DOCUMENTS 4,720,385   1/1988   Lembach .................................... 424/86

OTHER PUBLICATIONS

Wei, C–H et al "Affinity Cleavage At The Putative Metal–Binding Site Of Pigeon Liver Malic Enzyme By The $Fe^{2+}$–Ascorbate System,"0 *Biochemistry* 33, 7931–7936 (1994).

Hutchens, T.W. et al "Recognition Of Transition Metal Ions By Peptides: Identification Of Specific Metal–Binding Peptides In Proteolytic Digest Maps By UV Laser Desorption Time–Of–Flight Mass Spectrometry," *FEBS Letters* 10582 296:1, 99–102 (1992).

Chiou, S–H., "DNA–And Protein–Scission Activities Of Oscorbate In The Presence Of Copper Ion And A Copper–Peptide Complex," *J. Biochem.* 94, 1259–1267 (1983).

Misono, K.S., "Acidic pH–And Metal Ion ($Zn^{++}$ Or $Mn^{++}$–Dependent Proteolysis Of 140 kDa Atrial Natriuretic Factor Receptor In Bovine Adrenal Cortex Plasma Membranes: Evidence For Membrane–Bound Acidic Metalloendopeptidase," *Biochemical and Biophysical Research Communications* 152:2, 658–667 (1988).

*Primary Examiner*—Cecilia J. Tsang
*Assistant Examiner*—Bennett Celsa
*Attorney, Agent, or Firm*—Howrey & Simon

[57] ABSTRACT

The present invention relates to improved methods for the production of bioactive peptides. Specifically the present invention relates to improved methods for the chemical hydrolysis of proteins by organic acids in the presence of metallic ions.

14 Claims, No Drawings

METHODS FOR THE PREPARATION OF BIOACTIVE PEPTIDES BY PROTEIN HYDROLYSIS

FIELD OF THE INVENTION

The present invention relates to improved methods for the production of bioactive peptides via protein hydrolysis. Specifically the present invention relates to the use of organic acids and metallic ions in an improved method of protein hydrolysis that permits the recovery of bioactive peptides.

BACKGROUND OF THE INVENTION

Many biological processes, such as immune recognition, intracellular and extracellular signaling and communication, transcription, translation and enzyme catalysis result from the recognition and binding between a "ligand" and a "receptor." Typically, receptor molecules are protein molecules. Although ligand molecules may be lipid, carbohydrate, ionic or peptide in nature, peptide and protein ligands are of particular interest. Peptide and protein ligands comprise the majority of hormones, growth factors, enzymes, neuroactive molecules, transcription and translation factors and immune epitopes. The biological activity of receptors results from their capacity to bind with high specificity to a particular portion of region (i.e., "epitope") of the ligand.

Pharmaceutical agents which interact with ligands to either enhance or inhibit their biological activity are very desirable. Such molecules have the potential for alleviating the symptoms of genetic disease, or for curtailing biological processes such as inflammation and immune reaction in circumstances where such processes would be undesirable.

Two basic approaches to obtaining such agents have been employed. In the first approach, a library of random peptide fragments is produced and then screened to identify particular fragments capable of interacting with a receptor of interest. Such fragments can be produced either via chemical synthesis, or through recombinant DNA technology.

In one such method, recombinant bacteriophage have been used to produce peptide libraries having $10^6$–$10^8$ chemical entities (Scott and Smith, *Science*, 249:386–390 (1990); Cwirla, et al., *Proc. Natl. Acad. Sci.*, 87:6378–6382 (1990); Devlin, et al., *Science*, 249:404–406(1990)).

Methods that are primarily chemical, of which the Geysen method (Geysen, et al., *Molecular Immunology*, 23:709–715 (1986); Geysen et al., *J. Immuno. Method*, 102:259–274 (1987)) and the recent method of Fodor, et al., *Science*, 251:767–773 (1991) are examples, have also been used. The methodology of Geysen, et al. provides for a limited number of peptides ($10^3$–$10^4$) which are synthesized on polyethylene pins. The method of Fodor, et al., utilizes a "light-directed spatially addressable parallel chemical synthesis" technique. This technique is also limited by the relative lack of development of photochemical peptide synthesis methods.

The synthesis of a truly random peptide generally cannot be accomplished by simultaneously adding various amino acids into a single reaction vessel because the coupling rates for various amino acids differs tremendously during solid phase peptide synthesis (SPPS) (Ragnarsson, et al., *Acta Chem. Scand.* 25:1487, 1489 (1971); Ragnarsson, et al., *J. Org. Chem.* 39:3837–3842 (1974). For example, the coupling rate of Fmoc-glycine to a growing peptide is much faster than that of Fmoc-valine, probably due to steric hindrance from the bulky side chain of valine. If one were to mix all 20 activated eukaryotic L-amino acids with the resin during each cycle of coupling, the most rapidly reacting amino acids would be preferentially incorporated into the peptide, and equimolar ratios of each peptide species would not be obtained. Furthermore, each of the possible nucleophiles will have different reactivities.

Large scale parallel concurrent peptide synthesis techniques have however been developed. Houghton reported synthesizing hundreds of analogous peptides simultaneously in polypropylene mesh packets (tea bag method) (Houghton, *Proc. Natl. Acad. Sci. U.S.A.*, 82:5131–5135 (1985)). Berg, et al., *J. Am. Chem. Soc.* 111:8024–8026 (1989), reported a novel polystyrene-grafted polyethylene film support that is suitable for peptide synthesis in parallel fashion. Both techniques used standard Boc amino acid resin with the standard deprotecting, neutralization, coupling and wash protocols of the original solid phase procedure of Merrifield, *J. Am. Chem. Soc.* 85:2149–2154 (1963).

Furka, et al., 14th *International Congress of Biochemistry*, Volume 5, Abstract FR:013 (1988), described a method to produce a mixture of peptides by separately coupling each of three different amino acids, then mixing all of the resin. The procedure described by Furka, et al., provides no satisfactory method to isolate a peptide of interest from the plurality of peptides produced.

Unfortunately, the sheer number and variety of peptide sequences has encumbered the use of this approach. As a practical matter the chemical techniques of Geysen, Fodor, Houghton, Berg and Furka and their co-workers allow the synthesis and testing of only several hundred to a few thousand peptides at a time. Indeed, none of the above-described procedures enables the synthesis of such a quantity of different peptides at one time. Further multiplicity results by varying peptide chain length. Similarly, conventional peptide synthesis, such as that described in Stewart and Young (Solid Phase Synthesis, Second Edition, Pierce Chemical Co., Rockford, Ill. (1984) does not provide a method for the synthesis of thousands to millions of peptides at a time. Thus, in light of the millions of possible peptide sequences for even a small peptide (such as a pentapeptide), these techniques are quite limited.

The use of this approach is further complicated by the fact that the relevant bioactive peptide may comprise amino acid residues that are not contiguous within the primary sequence of the ligand, and hence are unlikely to be present in the peptide library.

In the second general approach to identifying and producing bioactive peptides, the ligand molecule is isolated, and fractionated in order to recover its bioactive peptide fragments. Typically, the use of this approach has been restricted to ligands that possess sequences sensitive to enzymatic cleavage or cyanogen bromide degradation. It thus has had very limited utility.

Enzymes can selectively cleave peptides and proteins. The enzyme most frequently applied for fragmentation is trypsin. It combines an enhanced rate of hydrolysis and a high degree of specificity (Bodansky, *Peptide Chemistry*, A Practical Textbook, 2nd Edition (Springer-Verlag, 1993)). Trypsin affects exclusively the bonds that follow the two basic amino acids, lysine and arginine. Additionally some cleavage after aromatic residues might be observed, which is not the consequence of the practically negligible inherent chymotrypsin-like activity of trypsin but rather of contamination of the enzyme preparation by chymotrypsin.

Trypsin can also be applied to cysteine containing peptides, because aminoethylation of the sulfhydryl group transforms the cysteine side chain to that of thialysine which, being similar to the lysine side chain, fits into the active site of trypsin. Accordingly cleavage of the chain will occur at the modified cysteine residue. Chymotrypsin is the second most preferred proteolytic enzyme. Its specificity is less absolute than that of trypsin. Primarily the bonds that follow phenylalanine, tyrosine and tryptophan are cleaved, but measurable hydrolysis takes place next to leucine and methionine residues as well. Other less specific enzymes, such as pepsin, papain or thermolysin can also be used to digest proteins.

A number of approaches have cleaved proteins in the presence of metal salts. Chiou, *Journal of Biochemistry,* 94: 1259–1267 (1983), described a protein cleavage activity that was associated with ascorbate in the presence of copper ions at pH 7.0. Similarly, Wei et al. *Biochemistry* 33: 7931–7936 (1994) described a protein cleavage activity associated with ascorbate in the presence of iron salts at pH 7.4.

Misono, *Biochemical and Biophysical Research Communications,* 152: 658–667 (1988), described the cleavage of a single disulfide bond in an atrial natriuretic factor by treating the protein with hydrochloric acid in the presence of zinc or manganese ions at pH 3.5. Unlike the above-described methods, the present invention provides methods for producing libraries of bioactive peptides by the hydrolysis of proteins using organic acids in the presence of metallic ions. It thus results in the production of a larger variety of peptide fragments than can be obtained through enzymatic cleavage.

SUMMARY OF THE INVENTION

The present invention relates to improved methods for the production of bioactive peptides. Specifically the present invention relates to improved methods for the production of bioactive peptides by the chemical hydrolysis of proteins by organic acids in the presence of metallic ions.

In detail the present invention provides a method for the production of a bioactive peptide from a protein containing the peptide, the method comprising:

(A) incubating the protein in the presence of (1) an organic acid and (2) a metallic ion, under conditions sufficient to permit the hydrolysis of peptide bonds of the protein, wherein the hydrolysis results in the production of the bioactive peptide, and (B) recovering the bioactive peptide from other peptides formed from the hydrolysis (a) of the protein.

The invention particularly concerns the embodiment of the above method in wherein the organic acid is selected from the group consisting of acetic acid, ascorbic acid, lactic acid, citric acid and malic acid, and/or wherein such organic acid is provided at a concentration of between about 5% (w/w) and about 20% (w/w), and more preferably between about 5% (w/w) and about 10% (w/w).

The invention also particularly concerns the embodiment of the above methods wherein the metallic ion is selected from the group consisting of calcium ions, zinc ions, copper ions, magnesium ions, molybdenum ions, chromium ions and nickel ions and/or wherein the metallic ions are present at a concentration of between about 0.05 molar and about 1.5 molar.

The invention particularly concerns the embodiment of the above methods wherein both such organic acid and such metallic ions are employed.

The invention also concerns a bioactive peptide produced from the process comprising:

(A) incubating a protein containing the peptide in the presence of (1) an organic acid and (2) a metallic ion, under conditions sufficient to permit the hydrolysis of peptide bonds of the protein, wherein the hydrolysis results in the production of the bioactive peptide, and (B) recovering the bioactive peptide from other peptides formed from the hydrolysis (a) of the protein.

The invention particularly concerns the embodiment wherein such peptide is capable of binding to a receptor, particularly if it attenuates (i.e., lessens or inhibits) or enhances a biological function of the receptor.

The invention also particularly concerns the embodiment wherein such peptide is capable of binding to an enzyme, particularly if it attenuates (i.e., lessens or inhibits) or enhances a catalytic activity of the enzyme.

DETAILED DESCRIPTION OF THE INVENTION

Definitions:

The term "organic acid" refers to any acid that comprises the elements oxygen, carbon and hydrogen, in any combination, and such elements may also be in combination with any other element.

The term "metallic ion" refers to any ion of any alkali metal, any alkaline-earth metal, any rare earth metal or any transition element.

The term "pure" is intended to denote that a material, such as a bioactive peptide is present in a preparation that lacks other peptide species. In contrast, the term "purified" is intended to denote a material, such as a bioactive peptide that is present in a preparation that contains other peptide species, but that lacks certain molecular species naturally present or present in a protein hydrolysate The term "bioactive peptide" refers to any peptide that has biologically activity. In particular, such bioactivity includes a capacity to bind to a receptor molecule, or a capacity to enhance or impair enzyme catalysis, cellular signaling, transcription, translation, or other cellular processes. The term "peptide" refers to a molecule having at least two amino acid residues bonded together through peptide bond(s).

The term "hydrolysis" as used herein is intended to refer to the cleavage of a peptide bond. The hydrolysis accomplished by the methods of the present invention is "non-random" in that it preferentially cleaves certain peptide bonds (e.g., the bonds between certain amino acid residue pairs of dipeptides or oligopeptides) more efficiently than others. In contrast, "random" hydrolysis cleaves the peptide bond between any pair of amino acids, or peptide, with equal efficiency.

General Methods:

The present invention relates to improved methods for the production of bioactive peptides. Specifically the present invention relates to improved methods for the production of bioactive peptides by the chemical hydrolysis of proteins by organic acids in the presence of metallic ions. The hydrolysis is not random, but involves the cleavage of only certain peptide bonds of a protein.

The proteins of the present invention may be from any source, whether naturally occurring or otherwise. Sources that contain animal or human proteins are particularly preferred. In a preferred embodiment, it is preferred that the source comprise a purified, or more preferably pure, preparation of such protein. However, it is also understood that the protein of the present invention may constitute a mixture of proteins, and that the methods of the present invention may be employed using such a mixture.

The bioactive peptides of the present invention may be of any length greater than one amino acid. In a preferred embodiment, the bioactive peptides of the present invention may contain from about 5 amino acids to about 75 amino acid residues, or more preferably, from about 5 to about 20 amino acid residues.

The chemical hydrolysis of the present invention may be carried out in the presence of any suitable organic acid. In a preferred embodiment of the present invention, the chemical hydrolysis may be carried in the presence of organic acids of 2–10 carbon atoms. In a preferred embodiment of the present invention, the chemical hydrolysis may be carried out in the presence of acetic acid, ascorbic acid, lactic acid, citric acid or malic acid. It is also understood that the chemical hydrolysis may be carried out in the presence of mixtures of more than one organic acid.

The chemical hydrolysis of the present invention may be carried out using a suitable organic acid at a concentration sufficient to promote partial hydrolysis of a protein of interest. In a preferred embodiment of the present invention, the chemical hydrolysis may be carried out in the presence of between about 5% (w/w) to about 20% (w/w) of such organic acids. In an even more preferred embodiment of the present invention, the chemical hydrolysis may be carried out in presence of between about 5% (w/w) to about 10% (w/w) of such organic acids. It is also understood that the chemical hydrolysis may be carried out in the presence of more than one organic acid and it is preferred that the combined concentrations of such organic acids be between about 5% (w/w) to about 20% (w/w).

The chemical hydrolysis of the present invention may be advantageously carried out at an acidic pH. In a preferred embodiment of the present invention, chemical hydrolysis may be advantageously carried out at an acidic pH of from about pH 4 to about pH 6, and more preferably, from about pH 4.5 to about pH 5.5. In an even more preferred embodiment of the present invention, chemical hydrolysis is carried out at an acidic pH of approximately pH 5.

The chemical hydrolysis of the present invention is advantageously carried out in the further presence of metallic ions. Metallic ions are the ions of metallic salts. In a preferred embodiment of the present invention, the chemical hydrolysis may be carried out in the presence of an ion of one or more of the following metals: calcium, cobalt, zinc, copper, magnesium, molybdenum, chromium, nickel, ruthenium, rhodium, silver, cadmium, iridium, platinum, gold or mercury. Calcium, cobalt, zinc, copper, magnesium, molybdenum, chromium, and nickel are particularly preferred.

The chemical hydrolysis of the present invention may be carried out in the presence of metallic ions at any concentration effective to promote peptide bond hydrolysis. In a preferred embodiment, the chemical hydrolysis may be carried out in the presence of metallic ions at a concentration of between about 0.05 molar to about 1.5 molar. In an even more preferred embodiment, the chemical hydrolysis may be carried out in the presence of one or more of the following metallic ions: calcium, zinc, copper or nickel at a concentration of between about 0.05 molar to about 1.5 molar.

The chemical hydrolysis of the present invention may be carried out for an appropriate length of time. In a preferred embodiment, the chemical hydrolysis of the present invention, is carried out for between about 10 hours and about 72 hours at room temperature or warmer.

The chemical hydrolysis of the present invention may be carried under appropriate conditions that produce greater than one peptide. In a preferred embodiment the chemical hydrolysis of the present invention may be carried under appropriate conditions that produce greater than 10 peptides. In more preferred embodiment of the present invention the chemical hydrolysis of the present invention may be carried under appropriate conditions that produce greater than 100 peptides. In an even more preferred embodiment of the present invention the chemical hydrolysis of the present invention may be carried under appropriate conditions that produce greater than 1,000 peptides. In an even more preferred embodiment of the present invention the chemical hydrolysis of the present invention may be carried under appropriate conditions that produce greater than 10,000 peptides. In the most preferred embodiment of the present invention the chemical hydrolysis of the present invention may be carried under appropriate conditions that produce greater than 100,000 peptides.

Use of the Peptides of the Present Invention:

The present invention provides a means for generating peptide fragments of a particular selected protein. In one embodiment, such fragments may be evaluated to identify bioactive fragments of the protein (i.e., fragments that exhibit a catalytic or binding characteristic of the intact protein). Such fragments may be used to immunize animals (or humans), so as to provide a source of antibody specifically reactive with the selected protein, or (in the case of proteins derived from infectious agents) to provide immunity from infection.

The peptides generated by the above-described methods may be associated with (i.e., bonded to or otherwise conjugated with) the metal ion employed in the protein hydrolysis. The peptides may be administered to an animal or human to provide a dietary source of such metal ion.

In an alternate embodiment, the metal ion employed in the protein hydrolysis may be detectably labeled (e.g., radioactive, paramagnetic, electron dense, etc. Such metal ion-peptides may be used to generally image organs or organ systems (such as the gastrointestinal tract or the circulatory system). In an alternative embodiment, bioactive peptide associated with the metal ion may be provided to tissue or other biological samples, or to live animals or humans to thereby provide a means for imaging the presence of cells or tissue that selectively bind the peptide. Thus, for example, if the protein being hydrolyzed is a binding ligand for a cancer-associated antigen, the metal ion-labeled bioactive peptides can be used to image cells and tissue in which such cancer-associated antigen is present. The molecules of the present invention may thus be used in the same manner as heterologous antibodies to cellular receptors or ligands, except that they lack the inherent immunogenicity of heterologous antibodies. As will be appreciated, metal ions having a toxic label (e.g., radioisotopes) may be used to deliver such toxin to tumor cells, etc.

What is claimed is:

1. A method for the production of a peptide fragment from a protein, said method comprising:

(A) incubating said protein at an acidic pH in the presence of
   (1) about 5% (w/w) to about 20% (w/w) of an organic acid and
   (2) a metallic ion at a concentration of about 0.05M to about 1.5M, under conditions sufficient to permit the hydrolysis of peptide bonds of said protein, wherein said hydrolysis results in the production of said peptide fragment, and (B) permitting said hydrolysis to occur.

2. The method of claim 1, wherein said organic acid is selected from the group consisting of acetic acid, ascorbic acid, lactic acid, citric acid and malic acid.

3. The method of claim 1, wherein said concentration of said organic acid is between about 5% (w/w) and about 10% (w/w).

4. The method of claim 1, wherein said metallic ion is selected from the group consisting of calcium ions, zinc ions, copper ions, magnesium ions, molybdenum ions, chromium ions, and nickel ions.

5. The method of claim 2, wherein said metallic ion is selected from the group consisting of calcium ions, zinc ions, copper ions, magnesium ions, molybdenum ions, chromium ions and nickel ions.

6. The method of claim 5, wherein the concentration of said organic acid is between about 5% (w/w) and about 10% (w/w).

7. The method of claim 1, wherein said acidic pH is about pH 4 to about pH 6.

8. The method of claim 1, wherein said acidic pH is about pH 5.

9. The method of claim 7, wherein said organic acid of claim 1 is selected from the group consisting of acetic acid, ascorbic acid, lactic acid, citric acid and malic acid.

10. The method of claim 7, wherein said metallic ion of claim 1 is selected from the group consisting of calcium ions, zinc ions, copper ions, magnesium ions, molybdenum ions, chromium ions, and nickel ions.

11. The method of claim 9, wherein said metallic ion of claim 1 is selected from the group consisting of calcium ions, zinc ions, copper ions, magnesium ions, molybdenum ions, chromium ions, and nickel ions.

12. The method of claim 1, wherein said incubation is carried out for between about 10 hours and about 72 hours at room temperature or warmer.

13. The method of claim 7, wherein said incubation of claim 1 is carried out for between about 10 hours and about 72 hours at room temperature or warmer.

14. The method of claim 11, wherein said incubation of claim 1 is carried out for between about 10 hours and about 72 hours at room temperature or warmer.

* * * * *